US005514094A

United States Patent [19]
Anello et al.

[11] Patent Number: 5,514,094
[45] Date of Patent: May 7, 1996

[54] COOLING SYSTEM FOR OCULAR INFUSION SOLUTION

[75] Inventors: Peter J. Anello, Orange; John E. Crum, Mission Viejo, both of Calif.

[73] Assignee: The Anello Corporation, Tustin, Calif.

[21] Appl. No.: 196,942

[22] Filed: Feb. 14, 1994

[51] Int. Cl.⁶ ........................................... A61M 1/03
[52] U.S. Cl. ..................................................... 604/113
[58] Field of Search ................... 604/113, 114, 604/291, 4; 607/96, 98, 99; 62/3.2, 3.7

[56] References Cited

U.S. PATENT DOCUMENTS

| | | | |
|---|---|---|---|
| 4,249,923 | 2/1981 | Walda | 62/3.2 |
| 4,476,685 | 10/1984 | Aid | 62/3.2 |
| 4,494,380 | 1/1985 | Cross | 62/3.2 |
| 4,532,414 | 7/1985 | Shoh et al. | 604/114 |
| 4,705,508 | 11/1987 | Karnavas et al. | 604/113 |
| 4,962,761 | 10/1990 | Golden | 607/96 |
| 5,097,829 | 3/1992 | Quisenberry | 604/113 |
| 5,154,661 | 10/1992 | Higgins | 62/3.2 |
| 5,180,896 | 1/1993 | Gibby et al. | 604/113 |
| 5,269,749 | 12/1993 | Koturov | 604/113 |

Primary Examiner—C. Fred Rosenbaum
Assistant Examiner—Manuel Mendez
Attorney, Agent, or Firm—Price, Gess & Ubell

[57] ABSTRACT

A cooling system including a thermoelectric module, a detachable chilling cassette unit, control electronics, and temperature sensors, the cooling system delivering an ocular infusion solution to an irrigation site at a desired temperature. The control electronics, in response to inputs from the temperature sensors, control the thermoelectric module which regulates the transfer of heat from the ocular infusion solution passing through the chilling cassette. The chilling cassette is reusable after autoclave sterilization.

17 Claims, 4 Drawing Sheets

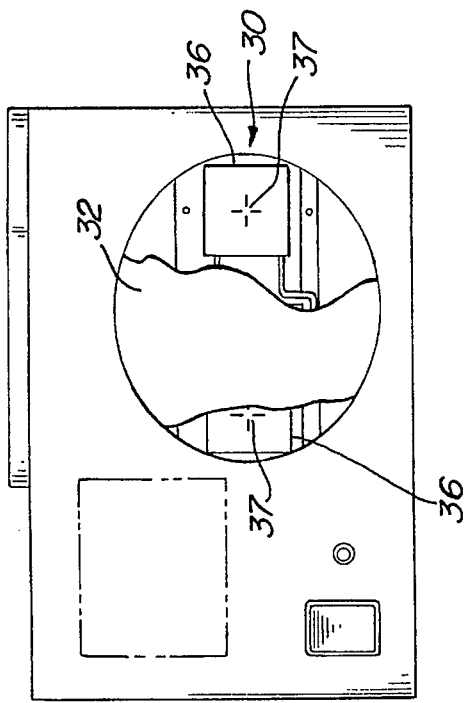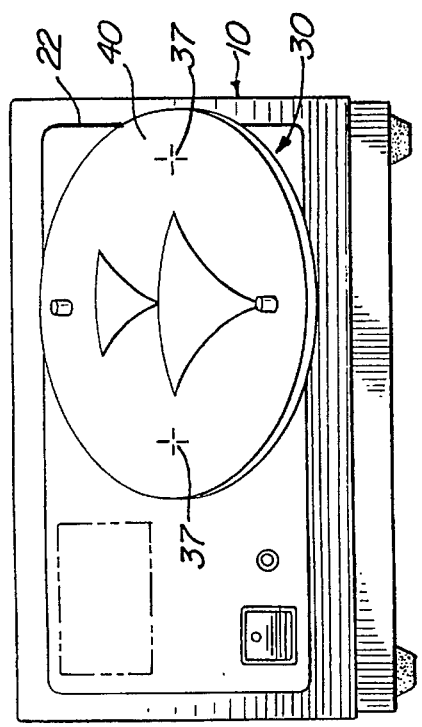
FIG. 4
FIG. 5

COOLING SYSTEM FOR OCULAR INFUSION SOLUTION

BACKGROUND OF THE INVENTION

1. Field of the Invention

The present invention relates to a cooling system for an ocular infusion solution and, more particularly, to a cooling system including a detachable, reusable chilling cassette which receives, cools, and dispenses ocular infusion solution to a destination site.

2. Description of Related Art

The art of transporting an ocular infusion solution to the human eye is generally cognizant of pumps and heat exchangers which may be used together for anterior chamber perfusion. Representative prior art in the field of transporting an ocular infusion solution is included below.

A 1983 British Journal of Ophthalmology article, "Ocular Hypothermia: Anterior Chamber Perfusion" by May et al., discloses the application of a saline solution to a rabbit eye wherein a heat pump and a temperature controller are utilized.

U.S. Pat. No. 2,124,293 teaches the broad concept of using a temperature controller to regulate the temperature of an infused fluid. Similarly, U.S. Pat. No. 4,249,923 discloses a refrigeration and delivery system for chilling a cardioplegic fluid to a predetermined temperature. U.S. Pat. No. 4,929,134 discloses a thermoelectric chiller in a cardiac application. Lastly, U.S. Pat. No. 4,734,091 teaches a filtered manifold apparatus and method of ophthalmic irrigation.

The need for an improved cooling system for ocular infusion solutions still exists, particularly in view of new surgical techniques which may probe deeper into the eye and require several hours of operating time. Surgical advances now permit surgery in the vitreous (posterior) chamber to remove opacified vitreous humor or to repair retinal detachment. Such operations require significant time, e.g., one to three hours, and large volumes of irrigating solution, e.g., 100–1000 ml.

During eye surgery and, particularly, during surgery which requires extended periods of time, proper electrolytic balance alone is insufficient to retain normal corneal thickness. To maintain proper corneal thickness and prevent cell damage, an irrigating solution, in addition to electrolytic balance, must provide metabolic support.

Although several cooling systems for infusion solutions exist, the art is still without an inexpensive cooling system that is simple to operate, features the added convenience of a detachable, reusable heat exchanger element (i.e., chilling cassette), permits the evacuation of air bubbles from the ocular infusion solution as the solution is being cooled, and delivers the infusion solution to the irrigation site at a controlled and predetermined temperature.

OBJECTS AND SUMMARY OF THE INVENTION

An object of the present invention is to provide a cooling system for an ocular infusion solution which is simple to operate and which delivers cooled ocular infusion solution at a controlled temperature.

Another object is to provide a cooling system which includes a detachable, reusable heat exchanger element in the form of a chilling cassette.

An additional object is to provide a cooling system which permits the evacuation of air bubbles from the ocular infusion solution while the infusion solution is being cooled.

Still another object is to provide a chilling cassette designed to evenly distribute the flow of the ocular infusion solution over the chiller cassette's thermal transfer membrane, thereby optimizing the chilling cassette's heat transfer capability.

The cooling system for the ocular infusion solution includes a housing with an open front portion, a means for delivering an ocular infusion solution from a reservoir to the cooling system, a means for chilling the ocular infusion solution to a predetermined temperature and for permitting the evacuation of air bubbles from the ocular infusion solution, and a means for dispensing the cooled ocular infusion solution from the cooling system. The chilling means is mechanically connected to the housing and positioned inside the housing to be visible through the front open portion. The chilling means includes a chilling cassette, a thermoelectric module, and a heat sink. As the ocular infusion solution passes through the cooling system's chilling cassette, the thermoelectric module transfers heat from the chiller cassette to the heat sink, in response to temperature control signals.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 4 is a partial cross-sectional front view of the chilling means of the cooling system;

FIG. 5 is a front view of the cooling system;

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a system for cooling an ocular infusion solution.

Figure 1:
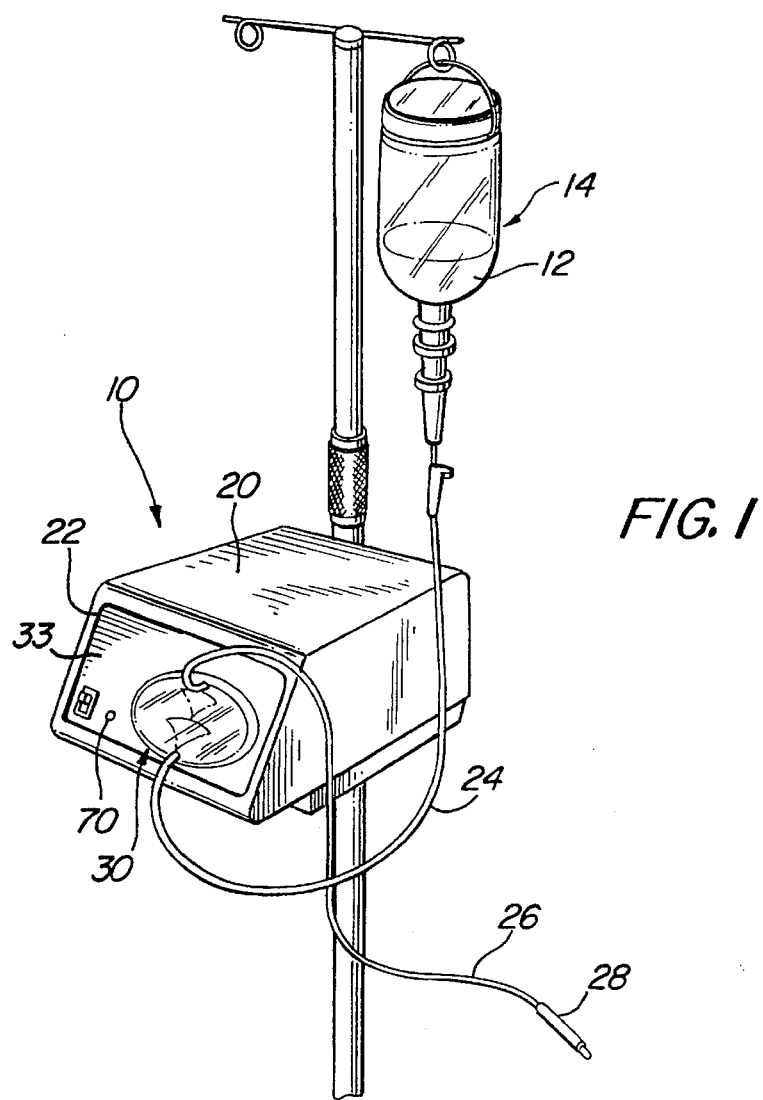
FIG. 1 is a schematic perspective of a cooling system for cooling an ocular infusion solution provided to the cooling system from a raised reservoir.

FIG. 1 shows a cooling system 10 for cooling an ocular infusion solution 12 delivered from a reservoir 14 by force of gravity to the cooling system 10. The cooling system 10 resides within a housing 20 which includes an open front portion 22. Reservoir 14 is pierced (i.e., "spiked") for connection to a delivery tube 24 which is attached, on respective opposing ends, to the reservoir 14 and the cooling system 10, thereby acting as a conduit through which the ocular infusion solution 12 is delivered to the cooling system 10. The height at which reservoir 14 is suspended over the cooling system 10 affects the rate at which the ocular infusion solution 12 enters the cooling system 10. The primary function of the cooling system 10 is to reduce the temperature of the ocular infusion solution 12. After passing through the cooling system 10, the cooled ocular infusion solution 12 exits the cooling system 10 from a dispensing tube 26 which is attached, on respective opposing ends, to the cooling system 10 and a distal tip 28.

Figure 2:
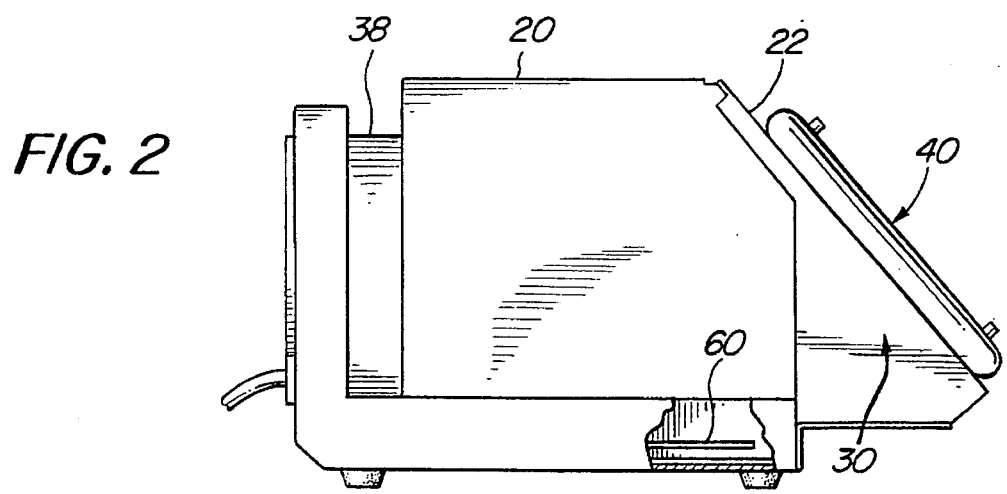
FIG. 2 is a partial cross-sectional side view of the cooling system.

FIG. 2 is a partial cross-sectional side view of the cooling system 10. A chilling means 30 (not entirely visible) is positioned inside and mechanically connected to the housing 20 such that the chilling means 30 may be seen through the open front portion 22 of the housing 20. The chilling means 30 receives and cools the ocular infusion solution 12.

Chilling means 30 includes a chilling cassette 40 which, as seen in FIG. 2, extends though open front portion 22 of housing 20. The chilling means 30 is shaped such that the chilling cassette 40 attached thereto appears to be tilted backward when viewed from the front side of the cooling system 10. Such a configuration maximizes the visibility of the chilling cassette 40 and permits the evacuation of air bubbles from the infusion solution 12 by the chilling cassette 40.

Cooling system 10, in the preferred embodiment shown in FIG. 2, further includes a fan 38 which cools chilling means 30 (more specifically, a heat sink included in chilling means 30). Control electronics 60, which regulate the cooling of the ocular infusion solution 12, as described below, are also included in the cooling system 10 and preferably reside within the housing 20.

Figure 3:
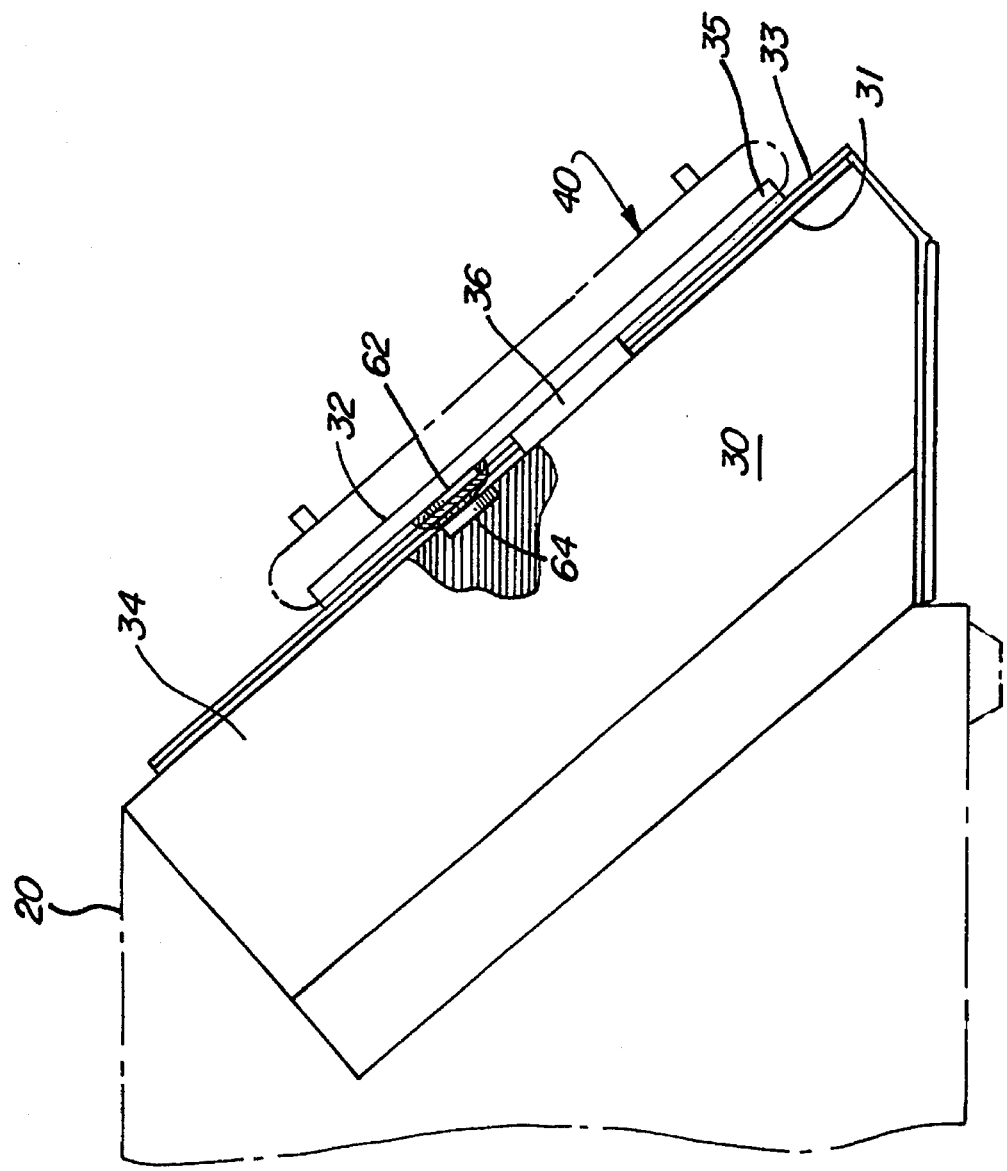
FIG. 3 is a partial cross-sectional side view of the chilling means of the cooling system.

FIGS. 3 and 4, respectively, are side and front partial cross-sectional views of the chilling means 30. Chilling means 30 includes a cold plate 32 (shown in FIG. 3) which is thermally connected to a heat sink 34 (shown in FIG. 3) via a pair of thermoelectric modules 36 (shown in FIG. 4) the positioning of the two thermoelectric modules 36 relative to the ellipse-shaped chilling cassette 40 is critical to maximizing the efficiency of the cooling system 10 in terms of thermal distribution and transmittance. In the preferred embodiment, the two thermoelectric modules 36 are respectively centered beneath the geometric foci 37 of the ellipse-shaped chilling cassette 40. Although two thermoelectric modules 36 are preferred, fewer or more thermoelectric modules may be used. Functionally, thermal energy is conducted through the cold plate 32 and the thermoelectric modules 36 to the heat sink 34. The heat sink 34 is preferably a finned aluminum extrusion which is cooled by a fan 38.

The following is a description of how chilling means 30 is assembled into housing 20. Heat sink 34 is first secured within housing 20 by screws, fasteners, or any other attaching means. As seen in FIG. 3, a first temperature sensor 62 and a second temperature sensor 64 are, respectively, attached to cold plate 32 and heat sink 34. The outputs of temperature sensors 62, 64 are provided to control electronics 60. Although two temperature sensors are illustrated in FIG. 3, the contemplated subject matter should in no way be limited to such a temperature sensing configuration. Additional temperature sensors may be incorporated into cooling system 10 and, for example, may be positioned within the posterior chamber to more accurately monitor the temperature of the cooled ocular infusion solution 12 at its destination site.

The assembly of chilling means 30 next requires that the thermoelectric module 36 (see FIG. 4) be attached to the heat sink 34. A thin layer of thermally conductive compound should be applied between the heat sink 34 and the thermoelectric module 36. Thereafter, assembly of the cooling system 10 involves the sequential attachment of a thermal blanket 31, an operator panel 33, and a thermal/moisture barrier 35 to the thermoelectric module 36 with the thermally conductive compound appropriately applied between the respective component interfaces. Multiple thermoelectric modules 36 may be utilized to increase the area of the heat-conducting path between the cold plate 32 and the heat sink 34. The cold plate 32 (which is preferably made of aluminum) is then attached to the resulting assembly with mounting screws of by other appropriate mounting means.

FIG. 5 is a front view of the cooling system 10 which shows the chilling means 30 exposed through the open front portion 22 of housing 20. FIG. 5 best illustrates a front view of the chilling cassette 40, which is detachably assembled to the chilling means 30. The assembly of chilling means 30 into housing 20 is completed by attaching the chilling cassette 40 to the cold plate 32, thereby thermally connecting the chilling cassette 40 to the thermoelectric module 36 and the heat sink 34. Chilling cassette 40 conducts heat from (thereby cooling) the ocular infusion solution 12 as the infusion solution 12 passes through the cooling system 10. Additionally, air bubbles (which are undesired in ocular infusion solutions) rise from the ocular infusion solution 12 as the ocular infusion solution 12 traverses the length of the chilling cassette 40. Natural displacement evacuation of air bubbles is an inherent advantage of cooling system 10.

Figure 6:
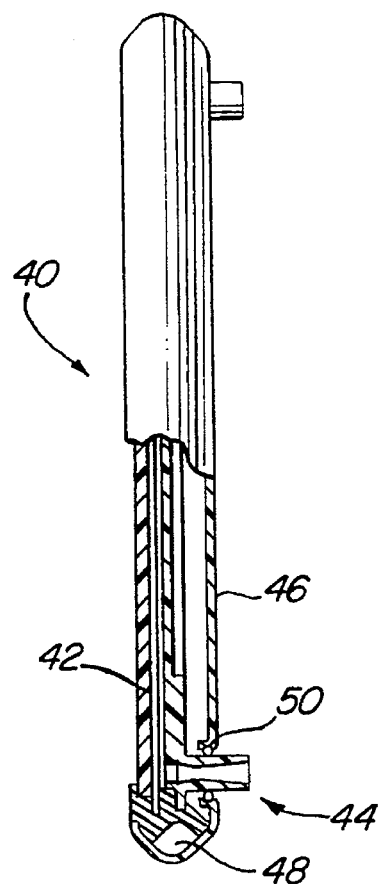
FIG. 6 is a partial cross-sectional side view of the chilling cassette included within the chilling means.

FIG. 6 is a partial cross-sectional side view of the chilling cassette 40. The chilling cassette 40 includes a thermal transfer membrane 42, preferably made of stainless steel, and a containment labyrinth 44, which together define a path through the chilling cassette 40. The performance of the chilling cassette 40 is optimized by minimizing the depth of the path, the depth being defined as a straight line extending normally from the thermal transfer membrane 42 to the inside wall of the containment labyrinth 44. Such a design choice maximizes the ratio of thermal transfer membrane 42 surface area contributing to the path over the volume of the path.

Thermal transfer membrane 42 and containment labyrinth 44 are held within a cassette shell 46 by retainer seal 48 and O-ring 50. A principal advantage provided by the chilling cassette 40 is that it is readily attached to and detached from the chilling means 30 (a.k.a. chilling head). Furthermore, the chilling cassette 40 is reusable after autoclave sterilization. An additional advantage of chilling cassette 40 is that its outer shell 46 acts as an insulator, thereby preventing condensation on the outer surface of the chilling cassette 40 and minimizing temperature increases within the chilling cassette 40.

Figure 7:
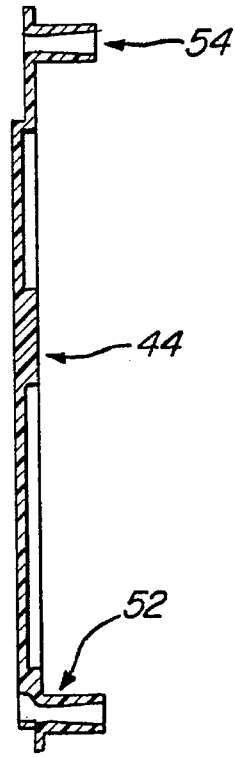
FIG. 7 is a cross-sectional side view of the containment labyrinth included within the chilling cassette.

As may be seen in FIG. 7, the containment labyrinth 44 includes a bottom inlet 52 through which the ocular infusion solution 12 enters into the chilling cassette 40, and a top outlet 54 through which the cooled ocular infusion solution 12 exits the chilling cassette 40. The ocular infusion solution 12 enters the cooling system 10 through the bottom inlet 52, moves upward through the containment labyrinth 44 by force of gravity, and exits the cooling system 10 through the top outlet 54. In a preferred embodiment, the delivery tube 24 is sized to fit securely around the bottom inlet 52, and dispensing tube 26 is sized to fit securely around the top outlet 54. Accordingly, the ocular infusion solution 12, within reservoir 14, is delivered to a desired irrigation site (such as the anterior or posterior chamber of the human eye) by sequentially passing through delivery tube 24, bottom inlet 52, containment labyrinth 44, top outlet 54, dispensing tube 26, and distal tip 28. A more detailed description of containment labyrinth 44 follows.

Figure 8:
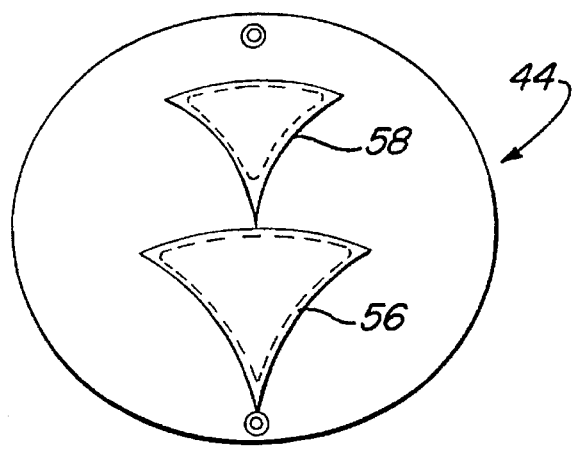
FIG. 8 is a front view of the containment labyrinth included within the chilling cassette.

FIG. 8 is a front view of the containment labyrinth 44 and shows that containment labyrinth 44 further includes a lower fluid splitter 56 and an upper fluid splitter 58. Fluid splitters 56, 58 and thermal transfer membrane 42 are all visible from the front of the cooling system 10 through cassette shell 46 which, in a preferred embodiment, is comprises of a transparent, polycarbonate material. Furthermore, the fluid splitters 56, 58 may be molded to the cassette shell 46. As the ocular infusion solution 12 enters the chilling cassette 40, it is evenly dispersed over the thermal transfer membrane 42 by the lower fluid splitter 56 and the upper fluid splitter 58. It has been found through computer modeling and experimentation that fluid splitters 56, 58, as pictured in FIG. 8, are optimally shaped and positioned to evenly disperse the ocular infusion solution 12 over the thermal transfer membrane 42. The optimized placement of the fluid splitters 56, 58, in conjunction with the aforedescribed positioning of the two thermoelectric modules 36 beneath the respective foci 37 of the ellipse-shaped chilling cassette 40, maximizes the rate at which the ocular infusion solution 12 is cooled.

The control electronics 60 (see FIG. 2) perform several functions, including temperature control of the ocular infusion solution 12. The electronics 60 are preferably embodied in a printed circuit board (PCB) within housing 20. As is known by those of ordinary skill in the art of control systems, a temperature control scheme for cooling system 10 may be realized in a variety of different ways. Temperature sensors 62, 64 provide input signals to the control electronics 60 which, in turn, control operation of the thermoelectric module 36. Ideally, such a control scheme activates audible and visual temperature sensor failure alarms, and disables the thermoelectric module 36 when the heat sink 34 overheats. A failure indicator 70, as seen in FIG. 1, should be positioned on the front side of cooling system 10 for maximum visibility. The following is a functional description of the heat transfer operation which is regulated by the control electronics 60.

The thermal transfer membrane 42 removes a quantity of thermal energy from the ocular infusion solution 12 as it passes upward through the chilling cassette 40. The thermal transfer membrane 42 (via its mechanical connection to the plate 32) provides a thermal path between the chilling cassette 40 to the cold plate 32. The thermal path continues from the cold plate 32 to the heat sink 34 via the thermoelectric module 36 which, as a part of the thermal path, transfers the quantity of thermal energy propagating therethrough. In a preferred embodiment, the thermoelectric module 36 is a Peltier-effect device which is controlled by the control electronics 60. The rate at which thermal energy is conducted though the thermoelectric module 36 to the heat sink 34 is regulated and limited by the control electronics 60.

The outputs of the temperature sensors 62, 64 are provided to the control electronics 60, which adjusts the polarity and/or magnitude of a control voltage which is applied to the thermoelectric module 36. The cooling system 10, with temperature sensors 62, 64 positioned as illustrated in FIG. 3, is adequate for anterior intraocular infusion wherein the ocular infusion solution 12 must be cooled to a particular temperature (preferably 7° C.) at the destination or irrigation site.

The change in temperature of the ocular infusion solution 12 from the cold plate 32 to the destination site is minimal when the ocular infusion solution 12 flows through the dispensing tube 28 at a sufficiently high rate. (Note that the cooling system 10 is intended to be used in conjunction with a phacoemulsification device. A typical emulsification average liquid flow rate is 25 mL/min.) Accordingly, the cooling system 10, with temperature sensors 62, 64 positioned as described above, is ideal for anterior intraocular infusion which is near the front portion of the eye. For posterior intraocular infusion, an additional temperature sensor may be positioned at an appropriate location in the eye or on the distal tip 26 to account for any temperature gradients across the eye.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A cooling system for cooling an ocular infusion solution delivered to the cooling system from a gravity fed reservoir, the cooling system comprising:

a housing;

means for delivering an ocular infusion solution from a reservoir to the cooling system; and chilling means, including a heat sink mechanically connected to the housing, for chilling the ocular infusion solution and for permitting the evacuation of air bubbles from the ocular infusion solution, the chilling means including a chilling cassette detachably assembled onto the housing, the chilling cassette comprising:

a thermally conductive surface for making contact with the ocular solution entering the chilling means;

a bottom inlet;

a top outlet; and a containment labyrinth partially formed by the thermally conductive surface, the ocular infusion solution entering the chilling cassette through the bottom inlet, following upward through the containment labyrinth, and exiting the chilling cassette via the top outlet.

2. A cooling system for cooling an ocular infusion solution delivered to the cooling system from a reservoir, the cooling system comprising:

a housing with an open front portion;

means for delivering an ocular infusion solution from a reservoir to the cooling system; and chilling means, mechanically connected to the housing and positioned inside the housing to extend through the open front portion, for chilling the ocular infusion solution to a predetermined temperature and for permitting the evacuation of air bubbles from the ocular infusion solution, the chilling means including a chilling cassette detachably assembled into the chilling means, the chilling cassette comprising:

a thermally conductive surface for making contact with the ocular solution entering the chilling means; a bottom inlet;

a top outlet; and a containment labyrinth partially formed by the thermally conductive surface, the ocular infusion solution entering the chilling cassette through the bottom inlet, flowing upward through the containment labyrinth, and exiting the chilling cassette via the top outlet.

3. The cooling system of claim 2 wherein the chilling means further comprises:

a thermoelectric device thermally connected to the thermally conductive surface; and a heat sink thermally connected to the thermoelectric device, the thermally conductive surface removing a quantity of thermal energy from the ocular infusion solution in the chilling cassette and conducting the thermal energy, via the thermoelectric device, to the heat sink for dissipation from the cooling system.

4. The cooling system of claim 3 wherein the thermoelectric device creates a thermal path between the thermally conductive surface and the heat sink, and wherein the cooling system further comprises:

means for dispensing the cooled ocular infusion solution from the cooling system to an irrigation site;

a plurality of temperature sensors positioned within the thermal path or proximate to the irrigation site, the temperature sensors outputting a plurality of temperature signals; and temperature control means for receiving the plurality of temperature signals and providing control signals to the thermoelectric device.

5. A cooling system for cooling an ocular infusion solution delivered to the cooling system from a reservoir, the cooling system comprising:

a housing with an open front portion;

means for delivering an ocular infusion solution from a reservoir to the cooling system;

chilling means, mechanically connected to the housing and positioned inside the housing to be visible through the open front portion, for chilling the ocular infusion solution to a predetermined temperature and for permitting the evacuation of air bubbles from the ocular infusion solution, the chilling means comprising:

an ellipse-shaped chilling cassette geometrically defined by two foci, the chilling cassette being detachably assembled into the chilling means, the chilling cassette comprising:

a thermally conductive surface for making contract with the ocular solution entering the chilling means;

a bottom inlet;

a top outlet; and a containment labyrinth partially formed by the thermally conductive surface, the ocular infusion solution entering the chilling cassette through the bottom inlet, flowing upward through the containment labyrinth, and exiting the chilling cassette via the top outlet;

two Peltier effect devices thermally connected to the thermally conductive surface; and a heat sink thermally connected to the Peltier effect device, the thermally conductive surface removing a quantity of thermal energy form the ocular infusion solution and conducting the thermal energy, via the Peltier effect device, to the heat sink for dissipation from the cooling system; and means for dispensing the cooled ocular infusion solution from the cooling system to an irrigation site.

6. The cooling system of claim 5 wherein the chilling means further comprises a cold plate to which the thermally conductive surface of the chilling cassette is attached, the cold plate providing a thermal path between the thermally conductive surface and the heat sink.

7. The cooling system of claim 6 further comprising:

a plurality of temperature sensors positioned within the thermal path or proximate to the irrigation site, the temperature sensors outputting a plurality of temperature signals; and temperature control means for receiving the plurality of temperature signals and providing control signal to the Peltier effect device.

8. The cooling system of claim 7 wherein the plurality of temperature sensors comprise:

a first temperature sensor attached to the cold plate; and a second temperature sensor attached to the heat sink.

9. The cooling system of claim 7 wherein the temperature control means comprises control electronics residing within the housing.

10. The cooling system of claim 5 wherein the two Peltier-effect devices are respectively positioned beneath the two foci of the chilling cassette.

11. The cooling system of claim 5 wherein the housing and the chilling means are shaped so that the chilling cassette, when attached to the cooling system, tilts backwards with the top outlet appearing to be behind the bottom inlet, when viewing the chilling cassette from a side of the housing containing the open front portion.

12. The cooling system of claim 1 wherein the containment labyrinth further comprises a fluid splitting means positioned within the chiller cassette for evenly distributing the ocular infusion solution over the thermally conductive surface, thereby enabling the chilling cassette to more efficiently conduct the quantity of thermal energy form the ocular infusion solution.

13. The cooling system of claim 12 wherein the fluid splitting means comprises a plurality of fluid splitters positioned centrally within the chiller cassette.

14. The cooling system of claim 5 wherein the chilling cassette is further comprised of a cassette shell insulating the containment labyrinth and wherein the plurality of fluid splitters are molded to the cassette shell.

15. The cooling system of claim 12 wherein the fluid splitting means comprises two fluid splitters positioned centrally within the chiller cassette.

16. The cooling system of claim 15 wherein the chilling cassette is further comprised of a cassette shell insulating the containment labyrinth and wherein the two fluid splitters are molded to the cassette shell.

17. A cooling system for controlling the temperature of an ocular injection fluid to be delivered by gravity flow from a storage reservoir to an eye of a patient comprising:

a heat exchange member for removing heat from the fluid;

a removable cassette member having a thermal transferring member attached to the heat exchange member, the cassette member includes fluid splitting means for directing the flow of fluid through the cassette member from a bottom inlet to a top outlet by gravity flow;

means for delivering the fluid to the bottom inlet of the cassette member from the storage reservoir; and means for removing the fluid from the top outlet of the cassette member for delivery to the eye, whereby the fluid is cooled and evacuation of air bubbles in the fluid is accomplished as the fluid traverses the fluid splitting means in the cassette member.

* * * * *